US008288158B2

(12) United States Patent  
McKnight et al.

(10) Patent No.: US 8,288,158 B2
(45) Date of Patent: Oct. 16, 2012

(54) STEM CELLS MODIFIED TO FACILITATE THREONINE CATABOLISM

(75) Inventors: Steven L. McKnight, Dallas, TX (US); Jian Wang, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 41 days.

(21) Appl. No.: 12/483,868

(22) Filed: Jun. 12, 2009

(65) Prior Publication Data

US 2010/0319078 A1 Dec. 16, 2010

(51) Int. Cl.
*C12N 15/79* (2006.01)
*C12N 15/00* (2006.01)
(52) U.S. Cl. ..................................... 435/325; 435/320.1
(58) Field of Classification Search .................. 435/325, 435/320.1
See application file for complete search history.

(56) References Cited

U.S. PATENT DOCUMENTS 5,082,670 A * 1/1992 Gage et al. .................... 424/520

OTHER PUBLICATIONS

Edgar (BMC Biochemistry, 3(19): 1-12, 2002.*
Edgar (BMC Genetics, 3(18): 1-13, 2002.*
Dale (BBA, 544: 496-503, 1978).*
Smith (Annu Rev Cell Dev Biol, 17: 435-462, 2001.*
Edgar et al (BMC Genomics, 6:32; p. 1-12, 2005, thereafter referred as Edgar 3).*
Capecchi et al (Trends in Genetics, 5L 5-76, 1996).*
Tallquist et al (Genesis 26:113-115 (2000).*

* cited by examiner

*Primary Examiner* — Gerald Leffers, Jr.
*Assistant Examiner* — Magdalene Sgagias
(74) *Attorney, Agent, or Firm* — Richard Aron Osman

(57) ABSTRACT

A mammalian cell comprising a recombinant, functional L-threonine 3-dehydrogenase (EC 1.1.1.103; TDH) gene, methods of making, and methods of use.

16 Claims, No Drawings

STEM CELLS MODIFIED TO FACILITATE THREONINE CATABOLISM

This invention was made with government support under Grant Number 5DP1OD00027605; awarded by the National Institutes of Health (NIH). The government has certain rights in the invention.

The field of the invention is stems cells modified to facilitate threonine catabolism.

INTRODUCTION

Embryonic stem (ES) cells are small, rapidly dividing cells endowed with the pluripotent capacity to form any and all cells present in the adult body. Cultured mouse ES cells measure only several micrometers in diameter, as compared to the 10-30 uM range typical of cultured somatic cells (1). The cell division cycle of ES cells is often shorter than rapidly dividing cancer cells, and approaches that of single celled microbial organisms. When deprived of leukemia inhibiting factor (LIF), mouse ES cells slow in growth rate, increase in size, form embryoid bodies and enter pathways leading to differentiation (2).

Wondering whether ES cells might exist in a unique metabolic state facilitating rapid growth, we surveyed the abundance of numerous common metabolites. Mouse ES cells, line E14, grown without feeder cells were exposed to organic solvents allowing soluble extracts to be subjected to a technique of liquid chromatography-mass spectrometry, designated LC-MS/MS, allowing multiple reaction monitoring of scores of metabolites (3). Parameters necessary for the detection of the two most abundant daughter ions for each metabolite upon collision-induced fragmentation were optimized so that metabolite identity and abundance could be simultaneously assessed.

The relative levels of individual metabolites prepared from ES cells were compared with embryoid body cells deprived of LIF for 3, 5 or 7 days. Three patterns of fluctuation in metabolite abundance were observed. One class consisted of metabolites that changed little as a function of the transition of ES cells into the differentiating cells present in embryoid bodies. Included in this class were many of the essential and non-essential amino acids. The second class consisted of metabolites present at a higher abundance in ES cells relative to differentiating cells. 5-aminoimidazolecarboxamide-R (AICAR), an intermediate in purine biosynthesis was at the top of this list, followed by acetyl-CoA and folic acid. The third class included metabolites that increased in abundance as a function of differentiation. Methyl-tetrahydrofolate (mTHF) was the most prominent member of this class, being nearly undetectable in ES cells, yet normalizing considerably in differentiating cells. A similar pattern of differentiation-associated elevation in abundance was observed for guanosine, adenosine, inosine and threonine.

Knowing that ES cells must replicate the genome at a prolific rate, it was sensible to observe that six of the metabolites changing most markedly in abundance as a function of ES cell differentiation are involved in the purine biosynthetic pathway (folic acid, mTHF, AICAR, guanosine, adenosine and inosine). The de novo synthesis of purine nucleotides requires that each purine base receive carbon atoms at two different steps along the pathway. The source of one-carbon metabolism for purine synthesis is formyl-tetrahydrofolate (4). This and the other two "charged" forms of tetrahydrofolate, methylene-tetrahydrofolate and methyl-tetrahydrofolate, represent the sole sources of one-carbon metabolism (5,6). Of particular interest is the fact that the AICAR intermediate in purine synthesis is located immediately downstream of one of the two single carbon donating steps in the pathway. Since AICAR was present at elevated levels in rapidly growing ES cells, and since folic acid and mTHF levels fluctuated significantly as a function of conversion of ES cells into embryoid bodies, we hypothesized that the demand for metabolic flux via one carbon metabolism might be unusually high in undifferentiated ES cells.

qPCR assays were performed on samples prepared from ES cells and seven tissues of the adult mouse to measure the levels of mRNAs specifying the fifteen enzymes most proximal to the pathway of one carbon metabolism (7). Such measurements revealed unusually accentuated, ES cell-specific expression of the gene encoding threonine dehydrogenase (TDH). We found the level of mRNA specifying synthesis of the TDH enzyme was roughly 1.000-fold higher in ES cells than any of the seven tissues that were assayed. In only one other case was it seen that the ES mRNA level of an enzyme exceed that of other tissues (the level of thymidylate synthase mRNA in ES cells was roughly two-fold higher than the levels observed in lung, intestine and testis).

The TDH enzyme performs the initial, rate-limiting step in an atypical form of threonine catabolism, wherein threonine is converted to glycine and acetyl-CoA. In eukaryotic cells the TDH enzyme is located within mitochondria. There it supplies acetyl-CoA for direct entry into the tricarboxylic (TCA) cycle, and likewise passes glycine to tetrahydrofolate charging via the glycine cleavage system (8). If the TDH enzyme was selectively active in undifferentiated ES cells, this might explain why threonine levels were reduced in ES cells compared with differentiating cells associated with embryoid bodies. High TDH enzyme activity might also explain why ES cells contained elevated levels of acetyl-CoA relative to embryoid body cells. To test this hypothesis, mitochondria were isolated from ES cells, assayed for the threonine-dependent conversion of NAD to NADH (9), and found to contain considerably higher TDH activity levels than 293T cells tailored to express an exogenous form of the TDH gene. It was likewise observed that TDH enzyme activity, TDH mRNA levels, and immunoreactivity to TDH-specific antibodies as detected by western blotting all declined precipitously as a function of differentiation of ES cells into embryoid bodies. The availability of TDH-specific antibodies (10) allowed immunohistochemical staining of ES cell colonies as a function of differentiation. Prior to LIF-withdrawal-induced differentiation, all cells in each ES colony stained positive for mitochondria-associated TDH. One day following LIF-withdrawal, TDH immunoreactivity was lost in differentiating cells located around the periphery of each colony, yet maintained in the small, centrally located cells. After prolonged LIF-withdrawal, all TDH-specific immunoreactivity was lost. These observations collectively raise the possibility that threonine catabolism via the TDH enzyme might be uniquely important to the growth and metabolic state of mouse ES cells.

Elegant studies of metabolic flux in rapidly growing bacterial cells have defined certain reaction pathways that flow at rates upwards of three to four orders of magnitude higher than other pathways of intermediary metabolism (11). The core circuitry of what has been termed the high-flux backbone (HFB) of metabolism includes the TDH enzyme. Whereas most amino acids are processed into biomass via translation during HFB metabolism, TDH converts the majority of threonine into glycine and acetyl-CoA. Since most microbial organisms, including yeast (12), are able to synthesize threonine de novo, the HFB pathway allows synthesis of sufficient amounts of threonine to satisfy the demands of both threonine catabolism to glycine and acetyl-CoA, as well its requirement for protein synthesis.

In order to test whether ES cells might deploy the TDH enzyme to adopt a metabolic state comparable to the HFB of bacterial cells, culture media were prepared individually deprived of each of the twenty amino acids. ES cells of the E14 line were plated and exposed to each of the "drop-out" culture media (13). After 36 h of exposure, normal ES colonies were observed to grow in all culture media except for that deprived of threonine. Colonies grown from either control media, or media individually lacking all amino acids except threonine, stained positively with the alkaline phosphatase marker prototypical of undifferentiated ES cells. Light microscopic inspection of ES cell colonies showed little or no difference in colony morphology, cell size or cell number as a function of media type. All of the media samples tested contained 10% fetal bovine serum. The serum component undoubtedly provides cells with residual levels of amino acids, as well as with serum proteins that can be hydrolyzed by cells to salvage amino acids for protein synthesis and other metabolic needs. These residual levels of amino acid supply are clearly sufficient for the growth of ES cells in all cases save for threonine deprivation. Virtually indistinguishable observations of acute threonine dependence were obtained on the CCE line of mouse ES cells, as well as the AOK-5P line of MEF-derived iPS cells. Moreover, just as was the case for the E14 line of ES cells, the CCE and AOK-5P lines were observed by immunofluorescence staining to express copious amounts of mitochondrial TDH enzyme.

When the same samples of drop-out media were tested for colony formation assays using HeLa cells, only leucine-deficient culture medium was observed to impede cell growth. Threonine-deficient medium supported HeLa colony formation as well as fully supplemented culture medium. Similar studies on mouse embryo fibroblast (MEF) cells and NIH 3T3 cells also failed to reveal differential sensitivity to threonine deprivation. MEF and 3T3 cell growth was instead exceptionally sensitive to cysteine deprivation. MEF cells grew indistinguishably in the presence of the 18 other drop out media, including that lacking threonine. 3T3 cells grew at a noticeably retarded rate in culture medium deprived of either arginine or leucine. Mild growth retardation was also observed for culture medium lacking methionine, glutamine, lysine, threonine, tryptophan, phenylalanine or valine. Finally, media samples deprived of serine, alanine, glycine, asparagine, histidine, tyrosine, aspartic acid, isoleucine or proline supported 3T3 cell growth to a level equivalent to fully supplemented culture medium. The unusual sensitivity to cysteine deprivation may indicate that some aspect of sulfur metabolism, perhaps relating to the production of glutathione, is of exceptional importance to the growth or survival of these partially differentiated, embryo-derived cell types. It can be clearly concluded, however, that the growth properties of Hela, MEF and 3T3 cells are not uniquely sensitive to threonine deprivation as was observed for mouse ES cells.

If TDH-mediated threonine breakdown in ES cells indeed supplies glycine to fuel one-carbon metabolism for enhanced purine biosynthesis, one might anticipate that deprivation of threonine would impede DNA synthesis. In order to test this hypothesis, ES cells were cultured in the presence of varying levels of threonine and exposed to brief labeling with $^3$H-thymidine (14). We found the incorporation of $^3$H-thymidine into DNA was reduced dramatically as a function of threonine concentration in the culture medium. Reduction of threonine supplementation to 30 uM was observed to partially inhibit $^3$H-thymidine incorporation into DNA. When threonine levels were dropped to 10 uM, DNA synthesis was impeded to an equally profound level as to that observed by complete elimination of threonine from culture medium (save for residual levels present in serum). By contrast, when HeLa cells were grown in culture medium supplemented with varying levels of threonine, DNA synthesis was unimpeded even under conditions of complete threonine deprivation.

Assuming that the TDH enzyme might allow ES cells to convert threonine into glycine as an alternative and theoretically enhanced mode of one-carbon metabolism, culture medium deprived of threonine was supplemented by elevated levels of glycine. Instead of the normal, 400 uM level of glycine, threonine-deficient medium was supplemented with 4 mM glycine. ES cells subjected to this threonine-deficient, glycine-enriched medium grew no better than those subjected to the threonine drop out medium itself. It is possible that ES cells are unable to deliver the supplemented glycine to mitochondria in order to feed the glycine cleavage system and folate charging. Alternatively, it is also possible that TDH-mediated production of acetyl-CoA is equally important to the HFB-like metabolic state. This alternative interpretation is consistent with the observation that among all metabolites that decline in abundance most precipitously as a function of the conversion of ES cells into differentiating embryoid bodies, acetyl-CoA was second only to the purine intermediate AICAR. In order to investigate these alternatives, we employed 3-hydroxynorvaline (3-HNV), a synthetic variant of threonine containing an extra carbon atom. It is known that the TDH enzyme can hydrolyze this threonine analog, yet instead of producing glycine and acetyl-CoA, catabolism of 3-HNV yields glycine and propionyl-CoA (15). ES cells were cultured in either normal or threonine-deficient medium supplemented with varying levels of 3-HNV. We found that not only did the analog fail to complement the absence of threonine, but it instead inhibited ES cell colony formation in the presence of normal culture medium. The inhibitory effect of 3-HNV was not observed on the growth of HeLa, MEF or 3T3 cells. These data indicate that mouse ES cells critically rely on TDH mediated production of both glycine and acetyl-CoA. Our data indicate that 3-HNV, a known TDH enzyme substrate, competes with the TDH enzyme in mitochondria of ES cells yielding only one of the two metabolites required of HFB metabolism.

The availability of 3-HNV as a cell-permeable threonine analog facilitated experiments using living mouse embryos. Before testing the effects of 3-HNV on early mouse embryo development, in situ hybridization and immunohistochemical staining assays were performed to investigate the expression pattern of both TDH mRNA and TDH enzyme (16). Both assays revealed staining patterns restricted to the inner cell mass (ICM) of blastocyst embryos. Knowing that the ICM represents the in vivo source of ES cells (17), we hypothesized that the early development of mouse embryos might be inhibited by 3-HNV. When administered at doses of 1 mM and 300 uM, 3-HNV blocked the conversion of morula-staged embryos into cavitated blastocysts (18). A more modest degree of inhibition was observed when embryos were incubated with 100 uM levels of the threonine analog. Complete rescue of normal development was observed, even at the 1 mM level of 3-HNV, when embryos were incubated in culture medium supplemented by 4 mM threonine. These studies indicate that ICM cells of the early mouse embryo, like cultured mouse ES cells, are critically dependent upon threonine catabolism.

Neither MEF nor 3T3 cell growth was selectively sensitive to threonine deprivation. Threonine-low (Tl) culture medium could thus be anticipated to selectively favor the growth of embryonic fibroblasts over ES cells. Unlike the threonine-dependence of ES cells, it was instead observed that both MEF and 3T3 cells failed to grow in cysteine-deprived medium. As such, threonine-high:cysteine-low (ThCl) culture media can selectively support ES cell growth relative to that of differentiating or differentiated cells of the early mouse embryo. To test this hypothesis, small numbers of ES cells were mixed and co-cultured with a vast excess of either MEF or 3T3 cells and exposed to culture media varied with respect to the level of supplementation of either threonine or cysteine. As expected, threonine deprivation severely limited the retrieval of ES clones from the mixed cultures under conditions in which both MEF and 3T3 cell growth was unimpeded. By contrast, deprivation of cysteine clearly favored the growth of ES cells relative to either MEF or 3T3 cells.

Mouse ES cells grow well in culture medium supplemented with standard levels of essential and non-essential amino acids, remaining continuously in a state of rapid, symmetric, self-renewing division where all cells are maintained in the ES state. ES cells derived from other species, even rodents as closely related as rats, have a strong tendency towards differentiation. So profound is the difference between mouse ES cells and ES cells derived from other organisms that there has not been a single reported incidence of success in the use of ES cells from any other species for homologous recombination and subsequent generation of an animal bearing targeted changes in the genome.

INTRODUCTION REFERENCES AND NOTES

1. B. Alberts et al., *Molecular Biology of the Cell* (Garland Publishing, Inc., New York, ed. March, 2007), pp. 1-1392.
2. A. G. Smith, *Annu. Rev. Cell Dev. Biol.* 17, 435 (2001).
3. B. P. Tu et al., *Proc. Natl. Acad. Sci. U.S.A.* 104, 16886 (2007).
4. L. Warren, J. M. Buchanan, *J. Biol. Chem.* 229, 613 (1957).
   H. Weissbach, A. Peterkofsky, B. G. Redfield, H. Dickerman, *J. Biol. Chem.* 238, 3318 (1963).
6. E. A. Phear, D. M. Greenberg, *J. Am. Chem. Soc.* 79, 3737 (1957).
7. Total RNA was extracted with RNA STAT-60 (Tel-Test) and converted into cDNA with oligo(dT) primer using the SuperScript first-strand synthesis kit (Invitrogen). PCR was performed on an AB 7900HT fast real-time PCR system (Applied Bioscience) using a TDH specific primer pair.
8. R. A. Dale, *Biochim. Biophys. Acta.* 544, 496 (1978).
9. TDH cDNA with an in-frame Flag tag sequence fused to the carboxyl terminus of the enzyme was cloned into mammalian expression vector pcDNA3.1 at EcoR1/Xho1 sites. The resultant vector was transfected into 293T cells using Lipofectamine 2000 reagent (Invitrogen). Stable transformants were selected in media containing 500 μg/ml G418 and characterized by western blotting analysis using anti-Flag antibody (Sigma). To extract mitochondrial protein, cells were homogenized in the buffer containing 10 mM Tris-HCl (pH 7.5), 250 mM sucrose and 2 mM EDTA on ice with a glass pestle douncer. Mitochondria were isolated from homogenates through a two-step differential centrifugation procedure at 600 and 11,000 g for 10 m each at 4° C. Mitochondrial protein was then extracted in 100 mM potassium phosphate buffer (pH 7.4) containing 0.1% NP-40, 10 mM DTT and 1× protease inhibitor cocktail (Sigma). TDH activity was determined by measuring the rate of formation of NADH at 25° C. The assay mixture contained 100 mM Tris-HCl (pH 8.0), 25 mM L-threonine, 5 mM NAD and 25 mM NaCl in a final volume of 1004 The reaction was initiated by the addition of mitochondrial protein extract, and absorbance of the reaction mixture at 340 nM was recorded continuously on a microplate reader.
10. Rabbit polyclonal antibodies to the mouse threonine dehydrogenase enzyme were produced using synthetic peptides. 5 mg of each peptide was conjugated to KLH carrier protein, mixed with complete Freund's adjuvant and injected into rabbits. Final bleeds containing TDH antibodies were taken after three additional immunizations in incomplete Freund's adjuvant.
11. E. Almaas, B. Kovacs, T. Vicsek, Z. N. Oltvai, A. L. Barabasi, *Nature* 427, 839 (2004).
12. J. L. Hartman, *Proc. Natl. Acad. Sci. USA* 104, 11,700 (2007).
13. Feeder-independent mouse E14Tg2A ES cells (BayGenomics) were cultured on gelatinized dishes in the Glasgow minimum essential medium (GMEM, Sigma) supplemented with 15% FBS (Hyclone), 100 μM MEM non-essential amino acids, 1 mM sodium pyruvate, 2 mM glutamine, 200 ug/ml penicillin, 100 ug/ml streptomycin (Stemcell Technologies), 100 uM 2-mercaptoenthnol and 1000 units/ml LIF (Chemicon). For embryoid body formation, $2 \times 10^6$ cells were grown in suspension on 100 mM low attachable dishes in 15 ml ES media without LIF. ES dropout media were prepared by omitting indicated amino acid from GMEM or non-essential amino acids. All component chemicals for dropout media preparation were obtained from Sigma.
14. After growth on 24-well plate for 1 day, mouse ES and HeLa cells were treated as indicated and metabolically labeled with [$^3$H]thymidine (2 μCi per well) for 3 hours. Following three washes with PBS, cellular macromolecules were precipitated by a 15 m incubation of cells on ice with 5% trichloroacetic acid, and then suspended in 0.5 N NaOH/0.5% SDS for liquid scintillation counting on a Beckman counter.
15. T. Kazuoka et al., *J Bacteriol* 185, 4483 (2003).
16. Peri-implantation mouse embryos were subjected to in situ hybridization by use of the methods of C. Chazaud et al., (*Dev. Cell,* 10, 615, 2006) and D. G. Wilkinson and M. A. Nieto, (*Methods Enzymol.* 225, 361, 1999). Sense and anti-sense probes were prepared from a full length cDNA clone of the mouse TDH gene. For antibody staining, peri-implantation embryos were fixed for 2 h in 4% paraformaldehyde in phosphate buffered saline (PBS). Following fixation embryos were rinsed 3 times for 5 m in Tris-buffered saline supplemented by 0.5% Tween-20 (TBST). Blocking was carried out for 1 h in 3% donkey serum in Tris-buffered saline supplemented with 0.1% Triton-X100. Primary antibody to the TDH enzyme (10) was diluted 1:500 in blocking buffer and incubated with embryos overnight at 4° C. Embryos were rinsed 3 times for 5 m in TBST. Secondary antibody, donkey anti-rabbit antibodies conjugated to Alexa488 was diluted 1:500 in blocking buffer and incubated with embryos for 2 h at room temperature. Embryos were rinsed 3 times for 5 m in TEST and visualized on an Axiovert fluorescence microscope (Zeiss) and photographed with a Hamamatsu Orca-ER camera.
17. F. A. Brook and R. L. Gardner, *Proc. Natl. Acad. Sci. USA* 94, 5709 (1997).
18. Eight-week old B6SJLF1 female mice were superovulated by a standard hormone regimen and mated to males of the same strain background. Fertilized one-cell eggs were cultured in microdrops of Brinster's medium for ovum culture (R. L. Brinster, *The Mammalian Oviduct*, University of Chicago Press, 419-444) under silicone oil in a 5% $CO_2$ humidified atmosphere for 48 h. Pre-compacted morulae were separated into groups of 20-25 embryos and placed into microdrops of Brinster's medium containing 1 mM, 300 uM, 100 uM, 30 uM and 10 uM 3-HNV with or without the addition of 4 mM threonine. Embryos were visually scored for developmental stages at 24 h and 48 h following the initiation of drug administration and photographed by light microscopy.

SUMMARY OF THE INVENTION

The invention provides a mammalian stem cell not in a human and comprising a recombinant, functional L-threonine 3-dehydrogenase (EC 1.1.1.103; TDH) gene. The invention encompasses all combinations of recited embodiments, including wherein:
  the TDH gene is a transgene;
  the TDH gene comprises an endogenous TDH allele operably-linked to a heterologous transactivator (such as LexPR transactivator), wherein expression of the gene is activatable (e.g. activated by RU486);
  the TDH gene is inactivateable, such as by a Cre-lox excision system, such as wherein a least a portion of the gene is flanked by loxP sites, and the cell further comprises a Cre recombinase;
  the TDH gene is heterologous to the cell;
  the TDH gene is heterologous mouse;
  the TDH gene is corrected human; and/or
  the TDH gene is over-expressed (compared with wild-type).

In particular embodiments, the cell is a primary explant cell, such as a fibroblast, liver stem cell, bone marrow cell, etc. In other embodiments, the cell is an embryonic stem cell, which may be mouse our non-mouse, such as human, rat, cow, horse, pig, goat, sheep, etc.

The invention also provides methods of making and using the subject cells, including methods comprising all combinations of the step(s) of:
  transfecting the cell or ancestor of the cell to form the TDH gene;
  growing the cell in a medium comprising (high) threonine.
  growing the cell in a medium comprising threonine, and detecting a resultant non-oncological expansion of the cell;
  growing the cell in a medium comprising threonine to obtain expanded cells, and introducing the expanded cells into a mammal;
  growing the cell in a medium comprising threonine, and genetically modifying (homologous gene targeting) the cell at a non-TDH target gene, and then introducing the cell into a mammal;
  growing the cell in a mammal.

The invention also encompasses:
  a cell culture comprising a subject cell;
  a mammal comprising a subject cell; and
  a mammalian cell transduced with exogenously-expressed TDH.

In another aspect, the invention provides methods materials and methods for growing cells, including:
  a mammalian, high-threonine cell culture medium;
  a method for promoting growth of a mammalian embryo, comprising the step of contacting the embryo with a high threonine medium; and
  a method for inhibiting growth of a mammalian embryo, comprising the step of contacting the embryo with a low threonine medium.

The invention also provides a method of modifying a cell, comprising the step of: (a) delivering inside a mammalian cell determined to be in need thereof functional L-threonine 3-dehydrogenase (EC 1.1.1.103; TDH), wherein the delivering is effected by: (i) recombinantly expressing the TDH in the cell or (ii) transducing the TDH into the cell, well as cells made by this method.

The invention includes all combinations of particular embodiments, including wherein:
  the TDH is expressed in the cell from a transgene encoding the TDH;
  the TDH is expressed in the cell from a recombined endogenous TDH gene;
  the TDH is recombinantly expressed in the cell, and the TDH expression is activateable or inactivateable;
  the TDH is recombinantly expressed in the cell, and the TDH expression is activatable, and the method further comprises the prior step of activating expression of the TDH;
  the TDH is recombinantly expressed in the cell, and the TDH expression is inactivateable, and the method further comprises the subsequent step of inactivating expression of the TDH;
  the TDH is transduced;
  the cell is a stem cell or primary explant cell; and/or the TDH is expressed in the cell and is: (i) heterologous mouse TDH, (ii) corrected human TDH, (iii) heterologous to the cell, and/or (iv) over-expressed.

This method of modifying a cell may further comprise combinations of steps such as:
  incubating the cell;
  detecting a resultant non-oncological expansion of the cell;
  introducing resultant progeny cells into a host mammal; and/or
  genetically modifying the cell by homologous, non-TDH, gene targeting, and then—growing the resultant cell into a mammal.

DESCRIPTION OF PARTICULAR EMBODIMENTS OF THE INVENTION

The invention provides methods and compositions for modifying cells, and resultant modified cell compositions. In one embodiment, the invention provides a mammalian cell not in a human and comprising a recombinant, functional L-threonine 3-dehydrogenase (EC 1.1.1.103; TDH) gene.

The gene encodes and expresses a functional, active TDH enzyme, and is artificially recombined, comprising a coding or transcription regulatory sequence heterologous to (not naturally present in) the cell. In one embodiment, the TDH gene is a transgene, which may encode a TDH that is homologous or heterologous to the cell, such a natural, wild-type mouse TDH enzyme expressed in a non-mouse target cell, such as a human or rat cell. The TDH coding sequence can come from any convenient organism, including archaebacteria (e.g. *P. furiosus*) bacteria (e.g. *E. coli*) and animals, particularly mammals including mouse, rat, goat, pig, and human (corrected), etc.

The transcript and encoded TDH are generally natural, wild-type sequence, however either may be modified, e.g. to optimize expression, provide functionality, etc. For example, wild-type encoded inactive human TDH may be corrected to functional, active human TDH, e.g. wherein the human gene mutations (i.e. the AG to GG splice acceptor mutations in exons 4 and 6, as well as the non-sense mutation within exon 6 wherein arginine codon 214 is replaced by a translational stop codon) are corrected to impart L-threonine 3-dehydrogenase catalytic activity to the expressed protein.

The TDH gene may also comprises an endogenous TDH coding sequence recombined and operably-linked with a heterologous, particularly non-TDH, transcriptional regulatory sequence, such as can be effected with transactivation or chromosomal promoter replacement. In an exemplary application, the TDH gene comprises an endogenous TDH allele operably-linked to a LexPR transactivator, wherein expression of the gene is activatable (e.g. activated by RU486).

The TDH expression maybe inducible, or temporally regulated or overexpressed (compared with wildtype or untransformed/transduced expression). In particular embodiments, the TDH gene is activateable or inactivateable. Methods for introducing activateable gene expression (e.g. binary, inducible gene expression systems using a promoter responsive to a synthetic activator) or inactivateable gene expression (e.g. Cre-lox methodologies) are known in the art. For example, where the TDH gene is inactivateable by a Cre-lox excision system, at least a portion of the TDH gene is flanked by loxP sites, and the cell further comprises a Cre recombinase. The invention also provides corresponding methods of use, such as comprising the step of activating or inactivating the TDH gene.

Suitable viral (e.g. retrovirus, adenovirus, etc.) and non-viral methods (lipoplexes, lipoplexes, dendrimers, electroporation etc.) for transforming the cell are well known in the art.

The invention provides a mammalian cell transduced with exogenously-expressed TDH, including corresponding methods of making and using such cell. Direct protein transduction may be effected, for example, with physical, electrical or chemical perturbation of the target cell membrane, e.g. microinjection, electroporation, polyethyleneglycol or salt precipitation, etc. Alternatively or in addition, the TDH may incorporate a cellular uptake tag (e.g. C-terminal polyarginine tag, HIV TAT) to increase transduction; see, e.g. Zhou et al. Cell Stem Cell 4, May 8, 2009, 1-4.

The recited cell is other than an oncogenic, immortalized, or passaged cell line cell, and is preferably not viral infected or transformed. In particular embodiments, the cell is a stem cell, particularly an embryonic stem (ES) cell, or a cell of a primary tissue explant.

In particular embodiments, the cell is a primary explants, organ or tissue cell, such as a fibroblast, bone marrow cell, skin, liver, pancreas, heart cell, etc. In other embodiments, the cell is an embryonic stem cell, which may be mouse our non-mouse, such as human, rat, cow, horse, pig, goat, sheep, etc.

In another aspect, the invention provides compositions and methods for growing cells with a mammalian, high-threonine cell culture medium. Subject compositions include formulations for making final medium compositions, including sterile, packaged (e.g. bottled) dry medium (e.g. powder form), concentrate, etc., which may comprise cultured subject cells, particularly non-human and/or non-murine ES cells. Typically the final medium comprises more than 400 uM supplemented threonine, preferably from 0.5, 1, 2, 4 or 10 mM to any greater amount of 2, 4, 10, 40 or 100 mM. To impose selective pressure on non-target cells, such as non-stem cells, the medium may be deficient in one or more component preferentially required by the non-target cells, such as low cysteine medium (e.g. less than 400 uM supplemented cysteine, preferably from 0.1, 0.4, 1, 4 or 10 uM to any greater amount of 1, 4, 10, 40 or 100 uM.

The TDH facilitates enhanced use of threonine as a metabolic fuel, and promotes growth of the cell. Accordingly, in particular embodiments the method comprises the step of: (b) detecting a resultant non-oncological expansion of the cell, and in particular application such as transplantation indications, optionally (c) introducing resultant progeny cells into a host mammal. For example, explanted cells, such as bone marrow cells may be expanded ex situ, and then reintroduced into the patient. In another embodiment, the target is a stem cell and the method further comprises the step of growing the cell into a tissue or non-human mammal. Optionally, the target cell may be genetically modified (e.g. by homologous (non-TDH) gene targeting) to create transgenic or a chimeric tissue or mammal.

By selectively promoting or inhibiting stem cell growth, the subject methods can be used to promote or discourage embryo development, and hence, fertility. For example, in one embodiment, the invention provides a method for promoting growth of a mammalian embryo (particularly livestock embryos), comprising the step of contacting the embryo with a high threonine medium (in utero or in vitro). In an alternative embodiment, the invention provides a method for inhibiting or discouraging growth of a mammalian embryo (particularly pest species), comprising the step of contacting the embryo with a low threonine medium (in utero or in vitro) or a TDH inhibitor (e.g. 3-hydroxynorvaline).

The invention encompasses all compositions, and combinations thereof, such as cells (particularly stem or ES cells), tissues (such as expanded bone marrow), organs (such as regenerated bladder) and non-human mammals (such as cow, horse, sheep, goat, rat, mouse, etc.) made by the subject methods.

EXAMPLES

Example 1

Transfection and Inducible Expression of Murine TDH Transgene in 293T and Human Primary Fibroblast Stem Cells TDH cDNA with an in-frame Flag tag sequence fused to the carboxyl terminus of the enzyme is cloned into mammalian RHeoSwitch expression system (Karns et al. BMC Biotechnol 2001, Jan., 11). The resultant vector is transfected into 293T cells using Lipofectamine 2000 reagent (Invitrogen); for transfecting human primary fibroblast cells (ATTC, CRL-2703) we use optimized electroporation using an exponential wave pulse of 250 V, 500 •F, 1000 •. A; see, Jordan et al., J Biomol Tech 19(5) 328-34. Stable transformants are selected in media containing 500 ug/ml G418 and characterized by western blotting analysis using anti-Flag antibody (Sigma).

Growth rate experiments are performed in a high-threonine, low-cysteine MEM (below) supplemented with 10% FCS. Induced TDH 293T and HPF cells demonstrate enhanced growth rates compared with control non-induced and sham-transfected cells.

Example 2

Transfection and Expression of Cre-loxP Inactivateable Murine TDH Transgene in Human Fibroblast Stem Cells and Other Cultured Human Stem and Non-Stem Cells A vector allowing transfection or virus-mediated infection of human stem cells or other cultured human cells is prepared to contain a suitable regulatory sequence to drive expression of either a repaired form of the hTDH gene or the TDH gene of a closely related mammal. This expression vector or virus is modified to contain loxP sites flanking all or an essential part of the TDH gene. When introduced by either transfection or infection, the expression vector facilitates expression of the TDH gene, allowing the transfected or infected human cell to express the TDH enzyme and functionally catabolize threonine as a means of specialized metabolism. At the point at which it is desired to eliminate TDH expression, the cells are exposed to Cre recombinase, allowing Cre-mediated elimination of the portion of the TDH gene flanked by loxP sites. This step can be carried out by infection of the cells with a virus expressing the Cre recombinase. Alternatively, the original expression vector containing the TDH gene flanked by loxP sites can be modified to contain an inducible form of Cre recombinase that is silent until the cells are exposed to the appropriate inducer. Said TDH expression vector or transducing virus may be modified to contain a drug selection marker necessary for selection of transfected or infected cells.

Example 3

Expression of Repaired Human TDG Gene or Murine TDH in Human Bone Marrow Stem Cells and Ex Vivo Expansion A vector allowing transfection or virus-mediated infection of human stem cells, such as bone marrow stem cells, is prepared to contain suitable regulatory sequences to drive expression of either a repaired form of the hTDH gene or the TDH gene of a closely related mammal. As specified in Example 2, this vector may be modified by loxP sites to allow expression of a functional TDH gene to be conditionally extinguished by Cre recombinase. Stem cells from the bone marrow of a human patient, or stem cells from any other other bodily source, are retrieved from the patient, then subjected to either transfection or virus-mediated infection in order to deliver the TDH gene into the explanted stem cells. The cells are then grown in threonine-supplemented culture medium as a means of expanding the stem cell population ex vivo. If needed, expression of the transfected or virally transduced TDH gene is extinguished by Cre-mediated recombination or any other means of eliminating expression of the TDH transgene before the cells are used for re-implantation in the human patient. Said TDH expression vector or transducing virus may be modified to contain a drug selection marker necessary for selection of transfected or infected cells. Ex vivo expansion can proceed conventionally.

Example 4

Expression of Murine TDH in Explant-Derived Human Hepatocytes, Non-Oncogenic Ex Vivo Expansion, Transplantation and Successful Engraftment Primary human hepatocytes are isolated from healthy parts of human liver fragments, collected during unrelated surgery. Cells are seeded in 96 well plates coated with rat tail collagen I at a density of $8 \times 10^4$ cells per well respectively. These cells are cultured at 37° C. in 5% $CO^2$ in complete William's E culture medium supplemented with 10% FCS, 2% penicillin-streptomycin, 1% sodium-pyruvate, 1% L-glutamine and 1% insulin-transferin-selenium.

TDH cDNA with an in-frame Flag tag sequence fused to the carboxyl terminus of the enzyme is cloned into mammalian RHeoSwitch expression system (Karns et al. BMC Biotechnol 2001, Jan., 11). The resultant vector is electroporated into the isolated hepatocytes using the Nucleofector™ system (Amaxa Biosystems, Koln, Germany) or with sterile NC solution having the following composition: 19.8 mM $KH_2PO_4$/80.2 mM $K_2HPO_4$/2 mM NaCl, pH 7.6. Freshly prepared 2 mM ATP and 5 mM reduced L-glutathione are added to NC solution just before use. Electroporation with NC solution is performed in a sterile cuvette (4 mm gap) with a single pulse of 1400 V, 70 µs followed immediately by a single pulse of 160 V, 37 ms delivered from a custom-made pulse generator. Eight µg endotoxin-free plasmid DNA TDH-Flag) is added to $4 \times 10^6$ viable hepatocytes in 0.2 ml electroporation solution before electrical pulsing.

Stable transformants are selected in media containing 500 ug/ml G418 and characterized by western blotting analysis using anti-Flag antibody.

The primary hepatocytes are expanded ex vivo in the high-threonine, low-cysteine MEM described below supplemented with 10% FCS and 10 nM RSL1 ligand. After 16-32× expansion (5-10 doublings) the RSL1 ligand is removed.

Acute liver injury is induced in C57 black/nude mice by administration of d-galactosamine (Ga1N) intraperitoneally at 0.7 g/kg body weight. Ga1N is dissolved in PBS, pH 7.4, at 100 mg/ml. Expanded hepatocytes are transplanted into the spleen of animals 36 hours after Ga1N treatment. Animals are anaesthetised under isoflurane, and $1 \times 10^6$ cells suspended in 200 µl of DMEM medium, are injected into the spleen over approximately 10-15 seconds. After securing haemostasis, the abdominal incision is closed and animals are monitored closely until recovery.

Engraftment of transplanted cells is confirmed by determining expression of human genes in transplanted mice. Livers of mice sacrificed one month after transplantation of expanded human hepatocytes demonstrate expression of each of human liver specific genes, including albumin, α1 antitrypsin, CK19, and α fetoprotein, as analyzed by RT-PCR using gene-specific primers.

Example 5

Transfection and Expression of Murine TDH Transgene in Rat ES Cells

A vector allowing transfection or virus-mediated infection of rat ES cells is prepared to contain appropriate regulatory sequences necessary to drive expression of either the rat TDH gene or that of a closely related mammal. As specified in Example 2, this vector may be modified by loxP sites to allow expression of a functional TDH gene to be conditionally extinguished by Cre recombinase or any other means of eliminating expression of the TDH transgene before the cells are used to reconstitute a living rat. Cells are prepared from a rat blastocyst embryo before or after the embryo has been transfected with the TDH expression vector, micro-injected with the THD expression vector, or infected with a virus facilitating transduced expression of the exogenous TDH gene. Said expression vector may be modified to contain a drug selection marker necessary for selection of transfected or infected cells. If rat cells prepared from blastocyst embryos are cultured before having been exposed to a microinjected, transfected or virus-transduced TDH gene, implantation of the exogenous TDH gene can be carried out in culture either by transfection, microinjection or virus-mediated transduction of the TDH gene. Cells are then cultured in the presence of exogenously supplied threonine as a means of endowing rat ES cells to sustain metabolic and growth capabilities comparable to that of mouse ES cells.

Example 6

Expression Mammalian TDH Transgene in Embryo-Derived Cells From Pigs, Horses, Sheep, Cows, Dogs, In Vivo Culture, Implantation and Production of Transgenic Animals

As specified in Example 4, a vector allowing transfection or virus-mediated infection of embryo cells derived from any species of animal is prepared to contain appropriate regulatory sequences necessary to drive expression of the TDH gene from the matching species, or that of a closely related mammal. As specified in Example 2, this vector may be modified by loxP sites to allow expression of a functional TDH gene to be conditionally extinguished by Cre recombinase or any other means of eliminating expression of the TDH transgene before the cells are used to reconstitute a living form of that species. Cells are prepared from the embryo of the relevant species before or after the embryo has been transfected with the TDH expression vector, micro-injected with the TDH expression vector, or infected with a virus facilitating transduced expression of the exogenous TDH gene. Said expression vector may be modified to contain a drug selection marker necessary for selection of transfected or infected cells. If embryo-derived cells are cultured before having been exposed to a microinjected, transfected or virus-transduced TDH gene, implantation of the exogenous TDH gene can be carried out in culture either by transfection, microinjection or virus-mediated transduction of the TDH gene. Cells are then cultured in the presence of exogenously supplied threonine as a means of endowing the ES cells of said species to sustain metabolic and growth capabilities comparable to that of mouse ES cells. Implantation and production of transgenic animals can proceed conventionally.

Example 7

Transfection and Expression of Corrected Human TDH Transgene in Human Fibroblast Stem Cells

The native human gene encoding TDH is non-functional by virtue of three inactivating mutations (A. J. Edgar, *BMC Genet.* 3, 18 (2002)). Although highly conserved in gene organization, as well as primary amino acid sequence of the predicted TDH open reading frame, the human TDH gene carries AG to GG splice acceptor mutations in exons 4 and 6, as well as a non-sense mutation within exon 6 wherein arginine codon 214 is replaced by a translational stop codon. Whereas polymorphic variation within the human population has been observed for the exon 4 splice acceptor mutation, with some individuals carrying the normal AG splice acceptor dinucleotide and others carrying the GG variant, all individuals genotyped to date carry both the splice acceptor and non-sense mutations in exon 6. rtPCR analysis of TDH transcripts expressed in human fetal liver tissue gave evidence of complete skipping of exon 4, and either complete skipping or aberrant splicing of exon 6. Given that exons 4 and 6 encode segments of the enzyme absolutely critical to its function, and that truncation via the non-sense codon at amino acid 214 would also yield an inactive variant, it appears that the native human gene is incapable of producing an active TDH enzyme. Remarkably, all metazoans whose genomes have been sequenced to date, including chimpanzees, appear to contain an intact TDH gene (K. D. Pruitt, T. Tatusova, D. R. Maglott, *Nucleic Acids Res* 35, D61 (2007)). Unless having evolved adaptive capabilities sufficient to overcome three mutational lesions, it would appear that humans are TDH-deficient. Conventional mutagenesis techniques are used to correct the AG to GG splice acceptor mutations in exons 4 and 6, as well as the non-sense mutation within exon 6 (restoring the arginine codon 214) to generate a functionally active human TDH.

We also designed, constructed and tested a synthetic functional human TDH with a restored arginine 214. Wild-type human TDH sequence was used to synthesize oligonucleotides, which were assembled and duplexed to make a synthetic human TDH gene (Blue Heron Biotechnology, Bothell, Wash.). TDH activity was determined by measuring the rate of formation of NADH at 25° C. The assay mixture contained 100 mM Tris-HCl (pH 8.0), 25 mM L-threonine, 5 mM NAD+ and 25 mM NaCl in a final volume of 100 ul. The reaction was initiated by the addition of mitochondrial protein extract, and absorbance of the reaction mixture at 340 nM was recorded continuously on a microplate reader.

Example 8

Transduction of Recombinant Murine TDH to Generate Induced Pluripotent Stem Cells

To generate recombinant TDH for our transduction experiments, we designed a transducibleTDH comprising a fused poly-arginine (11R) protein transduction domain fused to the C-terminus. This TDH is readily expressed in *E. coli* and then solubilized, refolded and further purified.

To confirm permeability and stability mouse embryonic fibroblast (MEF) cells are treated with the 11R-tagged recombinant TDH at various concentrations by adding the protein to the cell culture medium for 6-72 hr, and examining cell morphology and protein presence by immunocytochemistry; for applicable methods, see Zhou et al. (2009, Cell Stem Cell 4, May 8, 2009, epub, p. 1-4). These analyses confirm that 11R-tagged recombinant TDF readily enters cells at concentrations of 0.5 to 10 ug/ml within 6 hr. In addition, the transduced protein appears stable inside the cells for 48 hr.

We use this same transduction protocol to reprogram OG2/Oct4-GFP reporter MEF cells. The fibroblasts (initially seeded at the density of 50,000 cells/well in a six-well plate) are first treated overnight with the recombinant TDH at 8 ug/ml in mESC growth media enriched to 1 mM threonine, and optionally supplemented with 1 mM valproic acid (VPA), a HDAC inhibitor that improves reprogramming efficiency. After transduction, the cells are transferred onto irradiated MEF feeder cells and kept in mESC growth media until colonies emerge around day 30-35. The initial GFP+ colonies are subsequently passaged under conventional mESC growth conditions to yield piPSCs. The resultant cells are morphologically indistinguishable from classic mESCs, forming compact domed small colonies. They express typical pluripotency markers by immunocytochemistry and staining, including ALP, Oct4, Nanog, Sox2, and SSEA1, and RT-PCR analysis confirms endogenous expression of these pluripotency genes. Standard in vitro differentiation using embryoid bodies (EBs) or monolayer chemically defined stepwise differentiation, and in vivo chimerism assays confirm the developmental potential of the piPSCs, In particular, the piPSCs efficiently form EBs in suspension and differentiate into cells in the three primary germ layers, including endoderm, mesoderm and ectoderm derivatives, and the piPSCs efficiently incorporate into the inner cell mass of a blastocyst following aggregation with an eight-cell embryo, and lead to high-level chimerism with apparent germline contribution in vivo when the aggregated embryos are transplanted into mice, as confirmed by GFP genotyping in multiple three germ layer tissues of E13.5 fetuses and observation of Oct4-GFP+ cells in the gonad tissue in fetuses.

Example 9

High-Threonine, Low-Cysteine MEM

Dulbecco/Vogt modified Eagle's minimal essential medium (DMEM) 1×, Low Glucose, High Threonine, Low Cysteine.

| Component | mg/L |
| --- | --- |
| CaCl$_2$•2H$_2$O | 264.92 |
| Fe(NO$_3$)$_3$•9H$_2$O | 0.1 |
| KCl | 400.0 |
| KNO$_3$ | — |
| MgSO$_4$•7H$_2$O | 200.0 |
| NaCl | 6400.0 |
| NaHCO$_3$ | 3700.0 |
| NaH$_2$PO$_4$•H$_2$O | 125 |
| NaSeO$_3$•5H$_2$O | — |
| D-GLUCOSE | 1000.0 |
| PHENOL RED | 15.0 |
| SODIUM PYRUVATE | 110.0 |
| HEPES | — |
| L-ALANINE | — |
| L-ARGININE HCl | 84.0 |
| L-ASPARAGINE•H$_2$O | — |
| L-ASPARTIC ACID | — |
| L-CYSTINE | 4.8 |
| L-GLUTAMIC ACID | — |
| L-GLUTAMINE | 584.0 |
| GLYCINE | 30 |
| L-HISTIDINE HCl•H$_2$O | 42.0 |
| L-ISOLEUCINE | 105.0 |
| L-LEUCINE | 105.0 |
| L-LYSINE HCl | 146.0 |
| L-METHIONINE | 30.0 |
| L-PHENYLALANINE | 66.0 |
| L-PROLINE | — |
| L-SERINE | 42.0 |
| L-THREONINE | 475.0 |
| L-TRYPTOPHAN | 16.0 |
| L-TYROSINE | 72.0 |
| L-VALINE | 94.0 |
| D-BIOTIN | — |
| D-CALCIUM PANTOTHENATE | 4.0 |
| CHOLINE CHLORIDE | 4.0 |
| FOLIC ACID | 4.0 |
| i-INOSITOL | 7.2 |
| NICOTINAMIDE | 4.0 |
| PYRIDOXAL HCl | 4.0 |
| RIBOFLAVIN | 0.4 |
| THIAMINE HCl | 4.0 |
| VITAMIN B12 | — |

References: Dulbecco, R. and Freeman, G., Virology, 8:396, (1959); Smith, J. D. et al, Virology, 12:185, (1960); TCA Standards Committee, In Vitro, Vol. 6/2:93, (1970).

Example 10

High/Low Threonine Animal Feed Products Modulate Embryo Growth

Dietary threonine is reduced to curtail embryo growth in non-human mammals, and increased to enhance embryo growth in non-human mammals. For example, grain-based feed products are adjusted to about 0.04, 0.2, 0.4, 2 or 4 g/kg for low-threonine feed products, and to about 5, 6, 10 or 20 g/kg for a high-threonine feed product.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A mammalian stem cell not in a human and comprising a recombinant, functional L-threonine 3-dehydrogenase (EC 1.1.1.103; TDH) gene, wherein:
   the TDH gene is a transgene;
   the TDH gene comprises an endogenous-to-the-cell TDH allele operably-linked to a heterologous-to-the-cell transactivator, wherein expression of the gene is activated by an exogenous-to-the-cell activator;
   the TDH gene is heterologous to the cell;
   the TDH gene is human, wherein human gene mutations at the AG to GG splice acceptor mutations in exons 4 and 6, as well as the non-sense mutation within exon 6 wherein arginine codon 214 is replaced by a translational stop codon, are corrected to impart L-threonine 3-dehydrogenase catalytic activity to the L-threonine 3-dehydrogenase encoded by the TDH gene; or
   the TDH gene is over-expressed, as compared with a corresponding wild-type TDH gene, and comprises a coding or transcription regulatory sequence heterologous to the cell.

2. A mammalian stem cell not in a human and comprising a recombinant, functional L-threonine 3-dehydrogenase (EC 1.1.1.103; TDH) gene, wherein the TDH gene is a transgene.

3. A mammalian stem cell not in a human and comprising a recombinant, functional L-threonine 3-dehydrogenase (EC 1.1.1.103; TDH) gene, wherein the TDH gene comprises an endogenous-to-the-cell TDH allele operably-linked to a heterologous-to-the-cell transactivator, wherein expression of the gene is activated by an exogenous-to-the-cell activator.

4. The mammalian stem cell of claim 1, wherein the TDH gene is inactivatable by a Cre-lox system, wherein the gene is flanked by loxP sites, and the cell further comprises a gene encoding Cre recombinase.

5. The mammalian stem cell of claim 2, wherein the TDH transgene is a mouse TDH transgene.

6. A mammalian stem cell not in a human and comprising a recombinant, functional L-threonine 3-dehydrogenase (EC 1.1.1.103; TDH) gene, wherein the TDH gene is human, wherein human gene mutations at the AG to GG splice acceptor mutations in exons 4 and 6, as well as the non-sense mutation within exon 6 wherein arginine codon 214 is replaced by a translational stop codon, are corrected to impart L-threonine 3-dehydrogenase catalytic activity to the L-threonine 3-dehydrogenase encoded by the TDH gene.

7. A mammalian stem cell not in a human and comprising a recombinant, functional L-threonine 3-dehydrogenase (EC 1.1.1.103; TDH) gene, wherein the TDH gene is over-expressed, as compared with a corresponding wild-type TDH gene, and comprises a coding or transcription regulatory sequence heterologous to the cell.

8. The mammalian stem cell of claim 1, wherein the cell is a primary explant cell.

9. The mammalian stem cell of claim 1, wherein the mammalian stem cell is an embryonic stem cell.

10. A cell culture comprising the mammalian stem cell of claim 1.

11. The mammalian stem cell of claim 1, wherein the TDH gene is a mouse TDH gene and the cell is human and ex vivo.

12. The mammalian stem cell of claim 2, wherein the mammalian stem cell is an embryonic stem cell.

13. The mammalian stem cell of claim 3, wherein the mammalian stem cell is an embryonic stem cell.

14. The mammalian stem cell of claim 5, wherein the mammalian stem cell is an embryonic stem cell.

15. The mammalian stem cell of claim 6, wherein the mammalian stem cell is an embryonic stem cell.

16. The mammalian stem cell of claim 7, wherein the mammalian stem cell is an embryonic stem cell.

* * * * *